(12) United States Patent
Wass (10) Patent No.: US 11,926,385 B2
(45) Date of Patent: Mar. 12, 2024

(54) CYCLING EXERCISE SYSTEM, DEVICE, AND METHOD

(71) Applicant: IRL Incorporated, New York, NY (US)

(72) Inventor: Justin L. Wass, New York, NY (US)

(*) Notice: Subject to any disclaimer, the term of this patent is extended or adjusted under 35 U.S.C. 154(b) by 250 days.

(21) Appl. No.: 17/188,116

(22) Filed: Mar. 1, 2021

(65) Prior Publication Data

US 2022/0274663 A1 Sep. 1, 2022

(51) Int. Cl.
| | | |
|---|---|---|
| B62J 45/20 | (2020.01) | |
| A63B 24/00 | (2006.01) | |
| B62J 6/24 | (2020.01) | |
| G01S 19/19 | (2010.01) | |

(52) U.S. Cl.
CPC ........... B62J 45/20 (2020.02); A63B 24/0075 (2013.01); B62J 6/24 (2020.02); G01S 19/19 (2013.01); *A63B 2225/50* (2013.01)

(58) Field of Classification Search
CPC .. B62J 45/20; A63B 24/0075; A63B 2225/50; A63B 69/16
See application file for complete search history.

(56) References Cited

U.S. PATENT DOCUMENTS

| | | | |
|---|---|---|---|
| 4,141,630 A | 2/1979 | Emmons | |
| 5,839,990 A | 11/1998 | Virkkala | |
| 8,538,562 B2 | 9/2013 | Pryor et al. | |
| 9,352,183 B2 | 5/2016 | Quinn | |
| 9,868,028 B2 | 1/2018 | Shin | |
| 9,880,805 B1* | 1/2018 | Guralnick | G06F 3/0482 |
| 10,540,483 B2* | 1/2020 | Hardee | G16H 40/63 |
| 11,344,786 B2* | 5/2022 | Intonato | A63B 71/0686 |
| 2004/0239486 A1 | 12/2004 | Li et al. | |
| 2009/0063049 A1* | 3/2009 | Swisher | A63B 24/0062 701/469 |
| 2011/0133918 A1* | 6/2011 | Lee | B62J 50/22 340/436 |
| 2012/0253488 A1* | 10/2012 | Shaw | G06Q 10/04 700/91 |
| 2013/0268101 A1* | 10/2013 | Brammer | G01C 21/20 700/91 |
| 2016/0193499 A1* | 7/2016 | Kim | G09B 19/0038 434/247 |
| 2016/0375306 A1* | 12/2016 | Gu | G01S 19/42 701/430 |

(Continued)

FOREIGN PATENT DOCUMENTS

WO WO-2014124126 A1 * 8/2014 ......... A63B 22/0605

*Primary Examiner* — Jay Trent Liddle
*Assistant Examiner* — Alyssa N Brandley
(74) *Attorney, Agent, or Firm* — Olav M. Underdal; IDP Patent Services (57) ABSTRACT

A cycling exercise system includes: a bicycle, a server which includes a plurality of predetermined cycling course representations, and a device, including a processor, memory, input/output, and exercise controller, which enables the user to select a cycling course representation from the plurality of predetermined cycling course representations, such that the cycling exercise device directs the user along the selected cycling course representation and provides exercise instructions specific to course segments. Also disclosed is a method for cycling exercise, including: calculating available courses, selecting course, directing cyclist to course, and directing cyclist around course.

15 Claims, 9 Drawing Sheets

(56) References Cited

U.S. PATENT DOCUMENTS

| | | | |
|---|---|---|---|
| 2018/0043212 A1* | 2/2018 | Shirai | A63B 24/0062 |
| 2018/0236290 A1 | 8/2018 | Andersen | |
| 2019/0070461 A1* | 3/2019 | Werner | B62J 50/22 |
| 2019/0143194 A1* | 5/2019 | Evancha | A63B 24/0062 |
| | | | 482/4 |
| 2020/0001132 A1* | 1/2020 | Tuulari | B62J 45/41 |

* cited by examiner

FIG. 1A

Cycling Exercise System

FIG. 1B

Cycling Exercise System

FIG. 1C

Cycling Exercise System

FIG. 2

Cycling Exercise Server

FIG. 3

Cycling Exercise Device

FIG. 4

Cycling Course Data Structure

FIG. 5

FIG. 7
Application View

CYCLING EXERCISE SYSTEM, DEVICE, AND METHOD

CROSS-REFERENCE TO RELATED APPLICATIONS

N/A.

FIELD OF THE INVENTION

The present invention relates generally to the field of exercise system, and more particularly to methods and systems for mounting an exercise device on a bicycle.

BACKGROUND OF THE INVENTION

Although cycling is an effective and fun method of exercising, it is often difficult to find routes to ride. This is especially a problem for new riders, as there are not many predetermined routes in cities or towns. Most cyclists must discover their own routes.

However, discovering these routes takes time and often proves dangerous. Not knowing where they are going, cyclists can potentially get lost or wander onto high traffic roads with no protected bike lanes. It takes time for cyclists to find routes that align with their ideal factors such as safety, beauty, difficulty, and distance. The time and energy needed to find these routes can deter many cyclists from exploring their area or going on rides. Additionally, inexperienced cyclists may find it difficult to optimize the use of a bicycle's gears during their rides.

As such, considering the foregoing, it may be appreciated that there continues to be a need for novel and improved devices and methods for bicycle exercise systems.

SUMMARY OF THE INVENTION

The foregoing needs are met, to a great extent, by the present invention, wherein in aspects of this invention, enhancements are provided to the existing model of bicycle exercise systems.

In an aspect, a cycling exercise system can include:
a) A bicycle; and
b) A cycling exercise device, which can be mounted on the bicycle or can be worn by the user;
wherein the cycling exercise device can be configured to enable a user to select a selected cycling course representation from the plurality of predetermined cycling course representations on the cycling exercise server;
such that the cycling exercise device can be configured to direct the user along the selected cycling course representation and provide the user with exercise instructions and motivations specific to parts of the selected cycling course representation.

In a related aspect, the cycling exercise system can further include:
a) a cycling exercise server, which can be configured to store a plurality of predetermined cycling course representations;
wherein the cycling exercise device can be configured to retrieve the plurality of predetermined cycling course representations from the cycling exercise server.

In another related aspect, a cycling exercise server can include:
a) A processor;
b) A non-transitory memory;
c) An input/output component; and
d) A course database, which stores the plurality of predetermined cycling course representations; all connected via
e) A data bus.

In a further related aspect, a cycling exercise device can include:
a) A processor;
b) A non-transitory memory;
c) An input/output; and
d) An exercise controller, which is configured to direct the user along the selected cycling course; all connected via
e) A data bus.

In yet another related aspect, each cycling course representation in the plurality of predetermined cycling course representations can include:
a) A course name;
b) A course length;
c) A course difficulty rating; and
d) A list of course segments, wherein each course segment includes:
i. A segment identifier;
ii. A starting coordinate; and
iii. A list of associated exercises, each including:
1. An exercise name;
2. An exercise difficulty level;

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. In addition, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

Before describing the invention in detail, it should be observed that the present invention resides primarily in a novel and non-obvious combination of elements and process steps. So as not to obscure the disclosure with details that will readily be apparent to those skilled in the art, certain conventional elements and steps have been presented with lesser detail, while the drawings and specification describe in greater detail other elements and steps pertinent to understanding the invention.

The following embodiments are not intended to define limits as to the structure or method of the invention, but only to provide exemplary constructions. The embodiments are permissive rather than mandatory and illustrative rather than exhaustive.

In the following, we describe the structure of an embodiment of a system for cycling exercise 100 with reference to FIGS. 1A and 1B, in such manner that like reference numerals refer to like components throughout; a convention that we shall employ for the remainder of this specification.

Figure 1A:
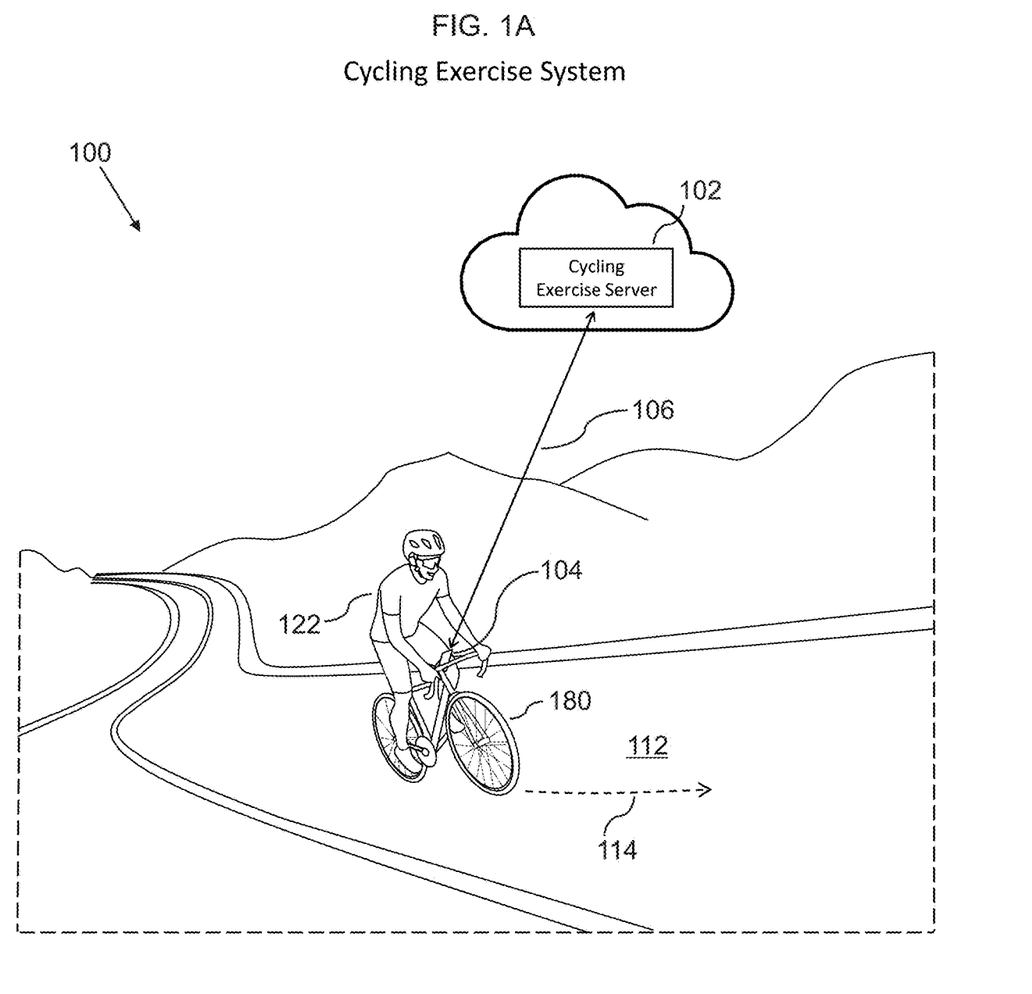
FIG. 1A is a perspective and in part schematic view of a cycling exercise system in use in a natural environment, according to an embodiment of the invention.
Figure 1B:
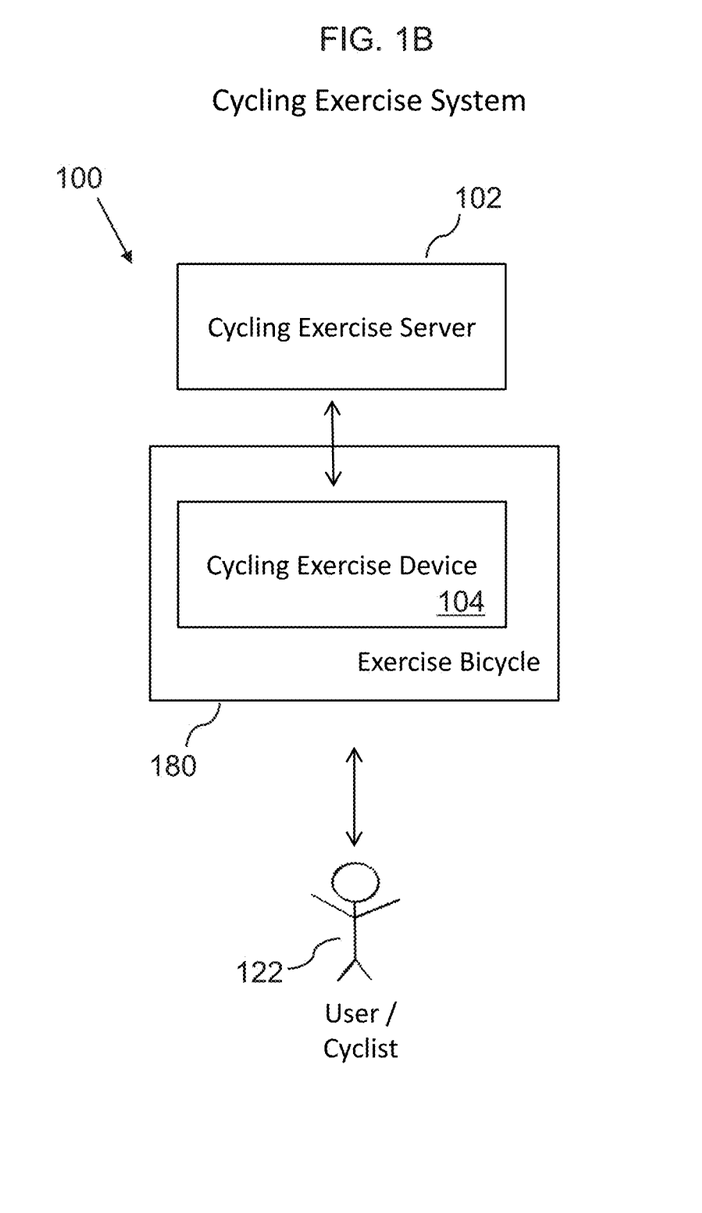
FIG. 1B is a schematic diagram illustrating a cycling exercise system, according to an embodiment of the invention.

In various embodiments, as shown in FIGS. 1A and 1B, a cycling exercise system 100 can include a cycling exercise device 104, that can be mounted on a bicycle 180 or can be worn by the user 122 (for example in a pocket of clothing of the user); such that the cycling exercise device 104 uses GPS location services to guide a user 122 along a predetermined cycling course representation and provides the user 122 exercise instructions and motivations specific to the part of the course they are on. Each predetermined cycling course representation 412 can have multiple workouts available with varying difficulties, trainers, and music genres. Thereby, the cycling exercise system 100 can provide a cycling workout that encourages users to exercise outdoors in the natural environment while providing a personalized training regime.

In an embodiment, as shown in FIGS. 1A, 1B, 1C, and 4, a cycling exercise system 100, 101 can include:
 a) A bicycle 180; and
 b) A cycling exercise device 104, which can be configured to be mounted on a bicycle 180 or can be worn by the user 122;
 wherein the cycling exercise device 104 can be configured to enable a user 122 to select a selected cycling course representation 412 from the plurality of predetermined cycling course representations 410 on the cycling exercise server 102;
 such that the cycling exercise device 104 can be configured to direct the user 122 along 114 the selected cycling course representation 412 (when the user 122 is riding on the bicycle 180 and cycling along 114 a physical route 112 that corresponds to the selected cycling course representation 412, as shown in FIG. 1A), and provide the user 122 with exercise instructions and motivations specific to parts of the selected cycling course representation 412.

Figure 1C:
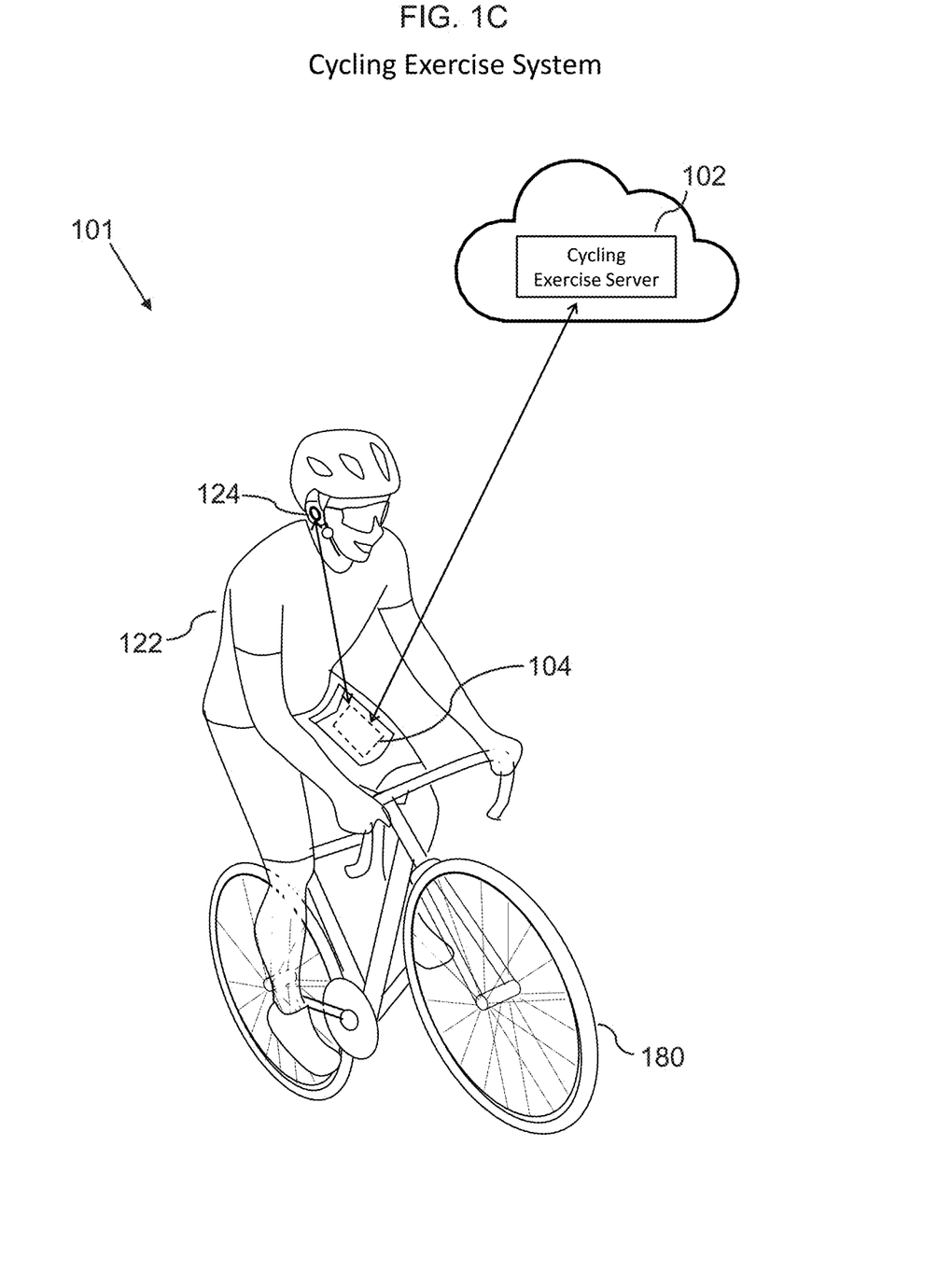
FIG. 1C is a perspective and in part schematic view of a cycling exercise, according to an embodiment of the invention.

In related embodiments, the cycling exercise device 104 can be configured to direct the user 122 along the selected cycling course representation 412 and provide the user 122 with exercise instructions and motivations specific to parts of the selected cycling course representation 412 by:
 a) providing audio instructions to the user 122, for example via:
  i. an earbud 124 that can be connected to the cycling exercise device 104 via a wired or wireless connection, as shown in FIG. 1C; or
  ii. a speaker 307 of the cycling exercise device 104; and/or
 b) providing visual instructions to the user via a screen 308 of the cycling exercise device 104.

In a related embodiment, as shown in FIG. 1C, a cycling exercise system 101 can be configured such that the cycling exercise device 104 is worn by the user 122, wherein the user can rely solely on audio instructions provided via an earbud 124 (or earbuds 124), which can be connected to the cycling exercise device 104 via a wireless connection, such as via BLUETOOTH™.

Figure 4:
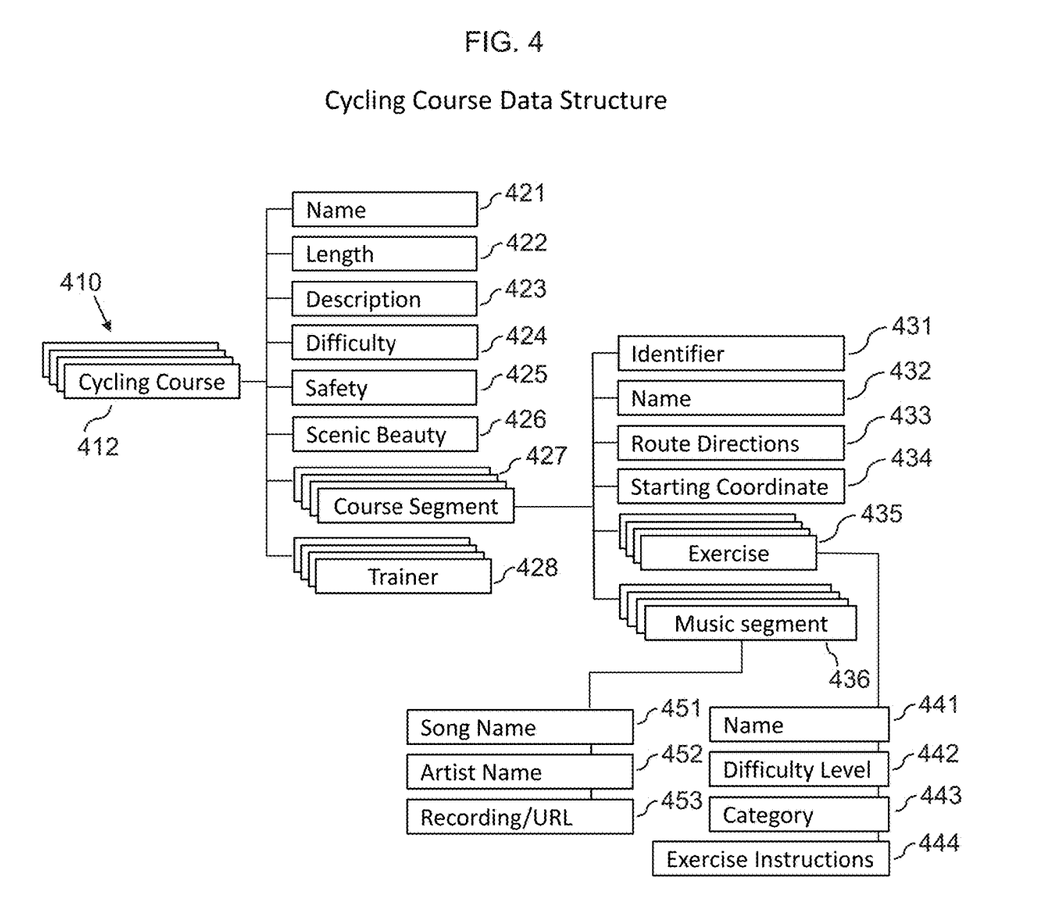
FIG. 4 is an schematic diagram illustrating a cycling course data structure, according to an embodiment of the invention.

In a related embodiment, as shown in FIGS. 1A, 1B, and 4, the cycling exercise system 100 can further include:
 a) a cycling exercise server 102, which can be configured to store a plurality of predetermined cycling course representations 410;
 wherein the cycling exercise device 104 can be configured to retrieve the selected cycling course representation 412 in the plurality of predetermined cycling course representations 410 from the cycling exercise server 102.

Figure 2:
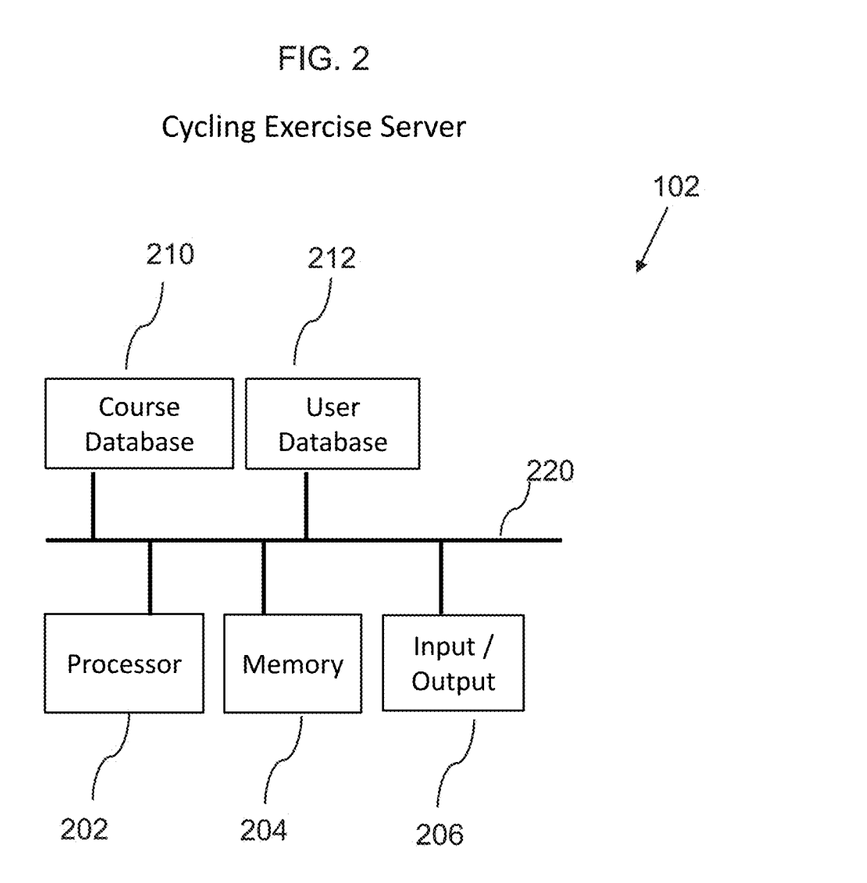
FIG. 2 is a schematic diagram illustrating a cycling exercise server, according to an embodiment of the invention.

In a related embodiment, as shown in FIG. 2, a cycling exercise server 102 can include:
 a) A processor 202;
 b) A non-transitory memory 204;
 c) An input/output component 206;
 d) A course database 210, which stores the plurality of predetermined cycling course representations; and
 e) A user database 212, which stores user information for a plurality of user; all connected via
 f) A data bus 220.

Figure 3:
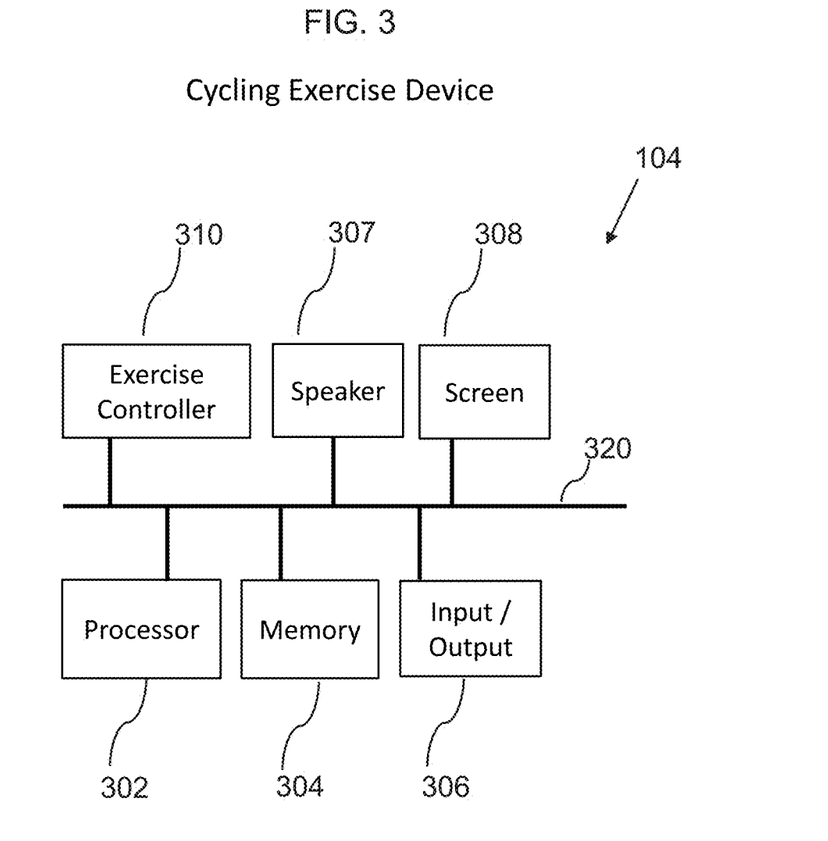
FIG. 3 is a schematic diagram illustrating a cycling exercise device, according to an embodiment of the invention.

In a related embodiment, as shown in FIG. 3, a cycling exercise device 104 can include:
 a) A processor 302;
 b) A non-transitory memory 304;
 c) An input/output 306;
 d) A speaker 307;
 e) A screen 308; and
 f) An exercise controller 310, which can be configured to direct the user 122 along the selected cycling course representation 412 and provide the user 122 with exercise instructions and motivations specific to parts of the selected cycling course representation 412; all connected via
 g) A data bus 320.

In related embodiment, as shown in FIG. 4, courses in the plurality of predetermined cycling course representations 410 can be chosen with consideration given to length, difficulty, scenic beauty and safety. Each course can have different options regarding difficulty, music, and trainers for the user to choose from. Each option available to users can feature unique GPS-based prerecorded instructions from trainers that will synchronize to the user's chosen musical option.

In a related embodiment, as shown in FIG. 4, each cycling course representation 412 in the plurality of predetermined cycling course representations 410 can include:
  a) A course name 421;
  b) A course length 422;
  c) A course description 423;
  d) A course difficulty rating 424;
  e) A course safety level 425;
  f) A course scenic beauty description 426;
  g) A list of course segments 427, wherein each course segment 427 includes:
     i. A segment identifier 431;
     ii. A segment name 432;
     iii. Segment instructions 433;
     iv. A starting coordinate 434;
     v. A list of associated exercises 435, each including:
        1. An exercise name 441;
        2. An exercise difficulty level 442;
        3. An exercise category 443; and
        4. associated exercise instructions 444, which can be visual, audio, audiovisual, and/or textual; and
     vi. A list of associated music segments 436, each including
        1. A song name 451;
        2. An artist name 452; and
        3. A song recording 453, which is playable by the exercise device 104, wherein the music recording 453 can be represented as a uniform resource locator 453 or an audio file, such as an MP3 file; and
  h) A list of trainers 428.

In a related embodiment, the exercise category 443 can include at least one of endurance, strength, interval, cardio, weight loss, etc.

Figure 5:
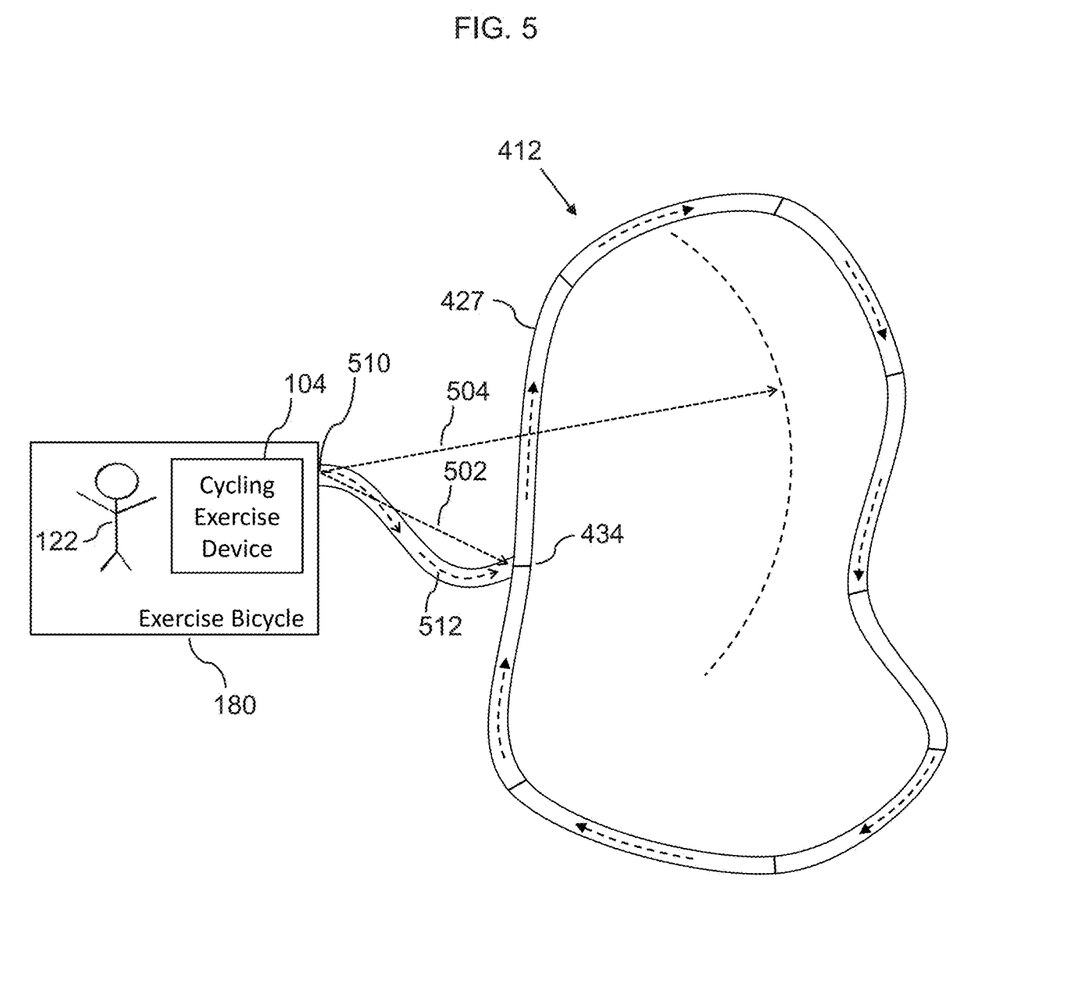
FIG. 5 is a schematic diagram illustrating directions for directing a cyclist to a selected course representation, according to an embodiment of the invention.

In a related embodiment, as shown in FIG. 5, the cycling exercise device 104 can be configured to calculate a list of available courses 410 from the plurality of predetermined cycling course representations 410, such that the available courses 410 within a predetermined maximum distance 504, such that a minimum distance 502 from a current location 510 to a closest starting coordinate 434 of a closest course segment 427 can be within the predetermined maximum distance 504, which can be found by a brute-force scanning of all course representations 412, and all associated course segments 427. The minimum distance 502 can be specified as either a bird's flight-distance or a route distance. The predetermined maximum distance 504 can be customizable as an option setting of the cycling exercise device 104.

In a further related embodiment, as shown in FIG. 5, the cycling exercise device 104 can be configured to enable the user to select a selected available course representation 412 from the list of available course representations 410, such that the cycling exercise device 104 can be configured to provide directions 512 from the current location 510 to the closest starting coordinate 434 of the closest course segment 427 of the selected available course representation 412.

Figure 7:
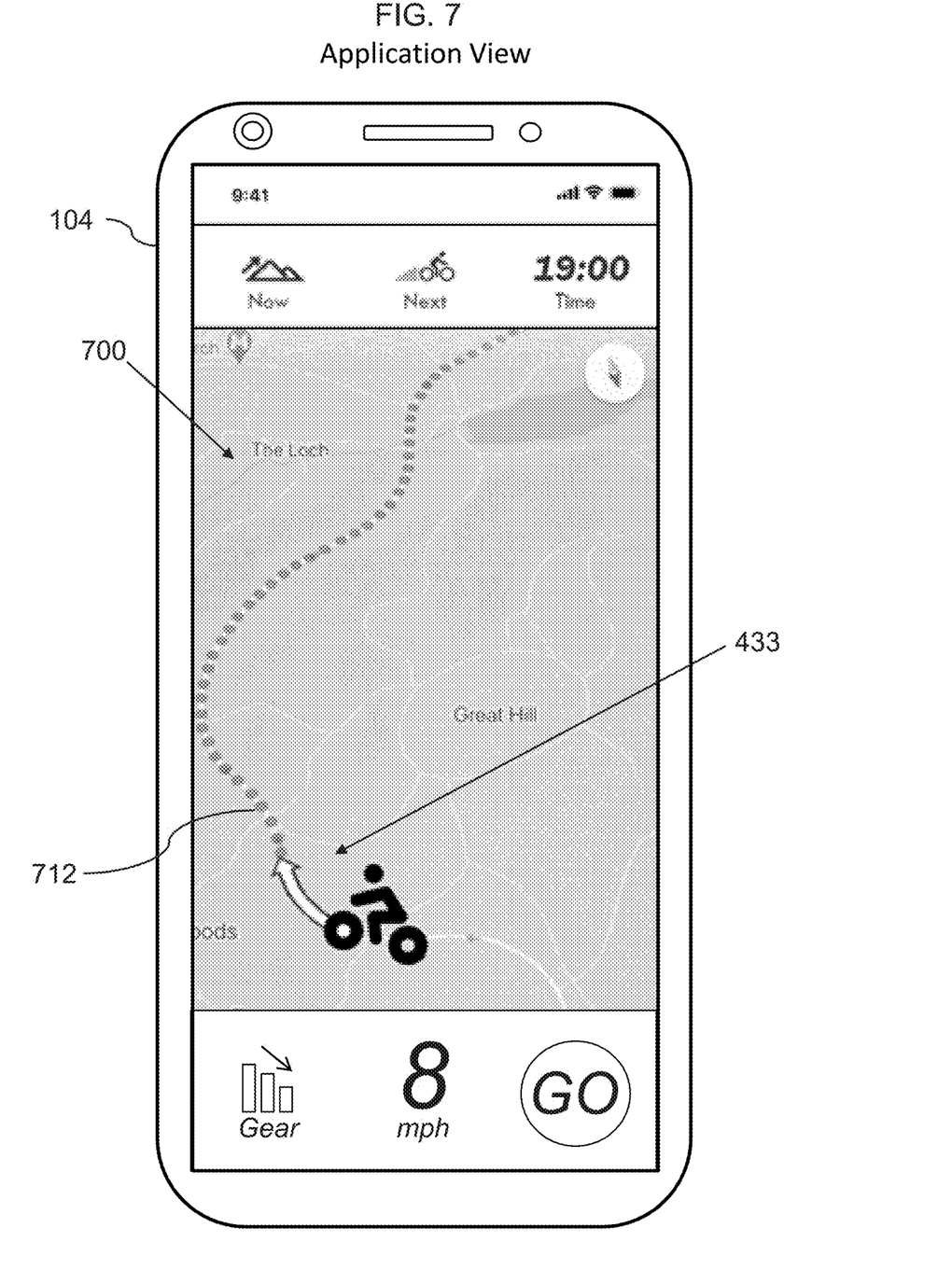
FIG. 7 is a schematic diagram illustrating an application view of the cycling exercise device, according to an embodiment of the invention.

In a related embodiment, FIG. 7 shows an application view 700 of the cycling exercise device 104, wherein the application view 700 depicts a visual presentation 712 of cycling directions/instructions 433 for a course segment 427 of a cycling course representation 412, which represents a physical course 112. Cycling directions/instructions 433 can be visual, audio, audiovisual, and/or textual.

In a related embodiment, marketing descriptions 423 for courses 412 in the plurality of predetermined cycling course representations 410 can for example include:
  a) Manhattan National Park: a 20-mile adventure that exemplifies the beauty and the beautiful ugliness of NYC all in one ride, Manhattan National Park takes users north through the hills of Central Park and the lively streets of Harlem to 125th St on the Hudson River. From there, users will ride along the water all the way to the southern tip of Manhattan and then back up the East River to 34th St, before concluding with a ride through the industrious streets of midtown. A scenic ride throughout, Manhattan National Park will take users past NYC icons like the Freedom Tower, 9/11 Memorial, Vessel of Hudson Yards, Whitney Museum, Oculus, USS Intrepid, Chelsea Piers and more! As the majority of the path is along the water, users will also have sweeping views of the Statue of Liberty, Brooklyn, Queens, and New Jersey as well as up close views of the Brooklyn, Manhattan and Williamsburg Bridges!;
  b) The Loop: a 6-mile ride through and around the famous Central Park Loop, The Loop takes users away from the city and puts them squarely into the city's playground! While this hilly course will be a challenge for any new rider's leg strength, IRL will help users up The Loop's hills by letting them know where to pick up speed and how to change gears to most effectively tackle these mini mountains! Meanwhile, advanced users will be able to take advantage of The Loop's ban of motor vehicles by working on their speed and cadence; and
  c) Five Bridges: What does a 14-mile path across 5 bridges and 3 boroughs equal? 2 tired legs and 1 satisfied IRLer! Users will work on their uphill endurance over and over again going up the Queensborough, Pulaski, Williamsburg, Manhattan, and Brooklyn Bridges, all while seeing NYC's glory in different boroughs.

In a related example embodiment, a 'The Loop Difficult Classic Rock Ride' 421 cycling course 412 can include a sequence of course segments 427, including:
  a) Segment N 427, 15 minutes 00 seconds into cycling course 412, such that:
     i. Music segment 436: 'Gimme Shelter' by The Rolling Stones begins playing;
     ii. Segment exercise instructions 444, including GPS-activated audio: "Finish strong and pedal through as you get to the top of this hill! This next downhill should be the fastest you go the whole ride, try to build up as much speed because Harlem Hill, our biggest climb, is next!";
  b) Segment N+1 427, 15 minutes 30 seconds into cycling course 412, such that:
     i. Music segment 436: 'Gimme Shelter' by The Rolling Stones continues playing;
     ii. Segment exercise instructions 444, including GPS-activated audio: "Gear up and keep going, the harder you work and faster you go now, the more your body will thank you on Harlem Hill!";
  c) Segment N+2 427, 16 minutes 00 seconds into cycling course 412, such that:
     i. Music segment 436: 'Gimme Shelter' by The Rolling Stones continues playing;
     ii. Segment instructions 433, including GPS-activated audio: "Keep your momentum going, your longest climb starts around the corner!";

d) Segment N+3 427, 16 minutes 30 seconds into cycling course 412, such that:
  i. Music segment 436: 'Gimme Shelter' by The Rolling Stones continues playing;
  ii. Segment exercise instructions 444, including GPS-activated audio: "Get out of the saddle and push when those quads start burning! Try to stay on your current gear for as long as you can, then gear down. This is where champions are made!";
e) Segment N+4 427, 19 minutes 00 seconds into cycling course 412, such that:
  i. Music segment 436: 'Gimme Shelter' by The Rolling Stones continues playing;
  ii. Segment exercise instructions 444, including GPS-activated audio: "You're almost there, only 30 more seconds until you're at the top. Gear down again if you need to, but try to keep this same pace up and finish strong!";
f) Segment N+5 427, 19 minutes 30 seconds into cycling course 412, such that:
  i. Music segment 436: 'Gimme Shelter' by The Rolling Stones fades out and ends and 'One Way Out' by The Allman Brothers Band begins playing;
  ii. Segment exercise instructions 444, including GPS-activated audio: "Good job! Now relax a bit and let the bike glide, we have rolling hills coming up so now is the time to recover".

In related embodiments, the cycling exercise device 104 can include configurations as:
a) A web application, executing in a Web browser on a mobile device;
b) A tablet app, executing on a tablet device, such as for example an ANDROID™ or IOS™ tablet device;
c) A mobile app, executing on a mobile device, such as for example an ANDROID™ phone or IPHONE™, or any wearable mobile device; and
d) An embedded application, executing on a processing device It shall be understood that an executing instance of an embodiment of the system for cycling exercise 100, as shown in FIGS. 1A and 1B, can include a plurality of cycling exercise devices 104, which are each tied to one or more users 122.

An executing instance of an embodiment of the system for cycling exercise 100, as shown in FIGS. 1A and 1B, can similarly include a plurality of cycling exercise servers 102.

Figure 6:
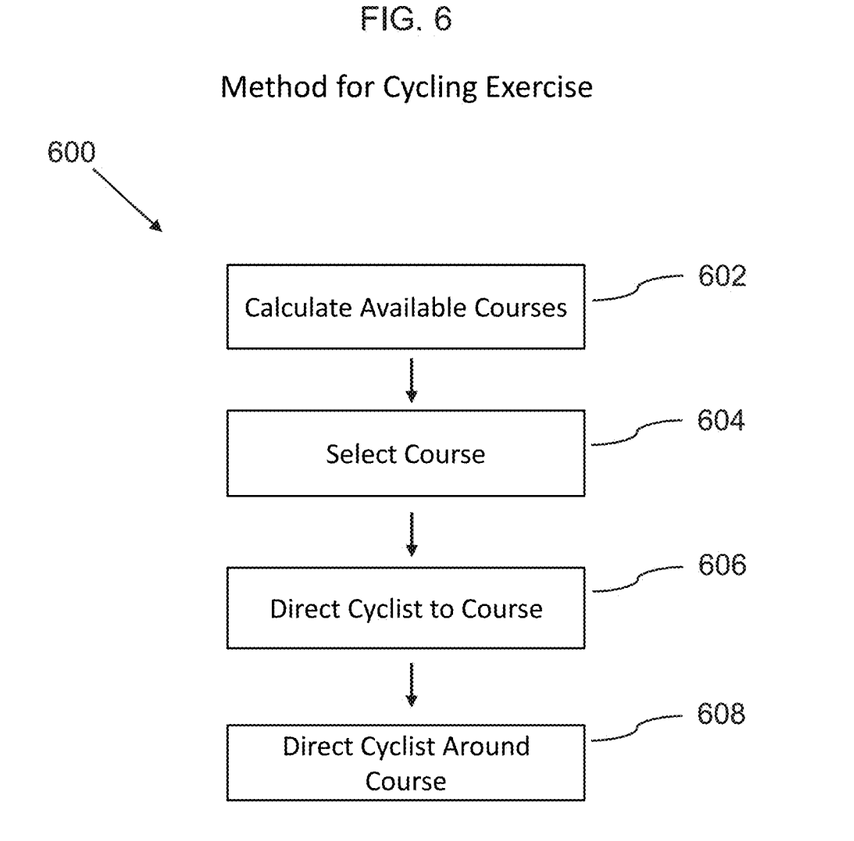
FIG. 6 is a flowchart illustrating steps that may be followed, in accordance with one embodiment of a method or process of cycling exercise.

In an embodiment, as illustrated in FIG. 6, a method for cycling exercise 600, can include:
a) Calculating available courses 602, wherein the cycling exercise device 104 calculates a list of available courses representations 410 within a predetermined maximum distance;
b) Selecting a course 604;
c) Directing cyclist to course 606, wherein the cycling exercise device 104 provides direction to the closest starting coordinate 434 of the closest course segment 427 of the selected course; and
d) Directing cyclist around course 608.

FIGS. 1A, 1B, 2, 3, 4, and 5 are block diagrams and flowcharts, methods, devices, systems, apparatuses, and computer program products according to various embodiments of the present invention. It shall be understood that each block or step of the block diagram, flowchart and control flow illustrations, and combinations of blocks in the block diagram, flowchart and control flow illustrations, can be implemented by computer program instructions or other means. Although computer program instructions are discussed, an apparatus or system according to the present invention can include other means, such as hardware or some combination of hardware and software, including one or more processors or controllers, for performing the disclosed functions.

In this regard, FIGS. 1A, 1B, 2, and 3 depict the computer devices of various embodiments, each containing several of the key components of a general-purpose computer by which an embodiment of the present invention may be implemented. Those of ordinary skill in the art will appreciate that a computer can include many components. However, it is not necessary that all of these generally conventional components be shown in order to disclose an illustrative embodiment for practicing the invention. The general-purpose computer can include a processing unit and a system memory, which may include various forms of non-transitory storage media such as random access memory (RAM) and read-only memory (ROM). The computer also may include nonvolatile storage memory, such as a hard disk drive, where additional data can be stored.

FIG. 1B shows a depiction of an embodiment of the cycling exercise system 100, including the cycling exercise server 102, and the cycling exercise device 104. In this relation, a server shall be understood to represent a general computing capability that can be physically manifested as one, two, or a plurality of individual physical computing devices, located at one or several physical locations. A server can for example be manifested as a shared computational use of one single desktop computer, a dedicated server, a cluster of rack-mounted physical servers, a datacenter, or network of datacenters, each such datacenter containing a plurality of physical servers, or a computing cloud, such as AMAZON EC2™ or MICROSOFT AZURE™.

It shall be understood that the above-mentioned components of the cycling exercise server 102 and the cycling exercise device 104 are to be interpreted in the most general manner.

For example, the processors 202 302 can each respectively include a single physical microprocessor or microcontroller, a cluster of processors, a datacenter or a cluster of datacenters, a computing cloud service, and the like.

In a further example, the non-transitory memory 204 and the non-transitory memory 304 can each respectively include various forms of non-transitory storage media, including random access memory and other forms of dynamic storage, and hard disks, hard disk clusters, cloud storage services, and other forms of long-term storage. Similarly, the input/output 206 and the input/output 306 can each respectively include a plurality of well-known input/output devices, such as screens, keyboards, pointing devices, motion trackers, communication ports, and so forth.

Furthermore, it shall be understood that the cycling exercise server 102 and the cycling exercise device 104 can each respectively include a number of other components that are well known in the art of general computer devices, and therefore shall not be further described herein. This can include system access to common functions and hardware, such as for example via operating system layers such as WINDOWS™, LINUX™, and similar operating system software, but can also include configurations wherein application services are executing directly on server hardware or via a hardware abstraction layer other than a complete operating system.

An embodiment of the present invention can also include one or more input or output components, such as a mouse, keyboard, monitor, and the like. A display can be provided for viewing text and graphical data, as well as a user interface to allow a user to request specific operations. Furthermore, an embodiment of the present invention may be connected to one or more remote computers via a network interface. The connection may be over a local area network (LAN) wide area network (WAN), and can include all of the necessary circuitry for such a connection.

In a related embodiment, the cycling exercise device 104 communicates with the cycling exercise server 102 over a network 106, which can include the general Internet, a Wide Area Network or a Local Area Network, or another form of communication network, transmitted on wired or wireless connections. Wireless networks can for example include Ethernet, Wi-Fi, BLUETOOTH™, ZIGBEE™, and NFC. The communication can be transferred via a secure, encrypted communication protocol.

Typically, computer program instructions may be loaded onto the computer or other general-purpose programmable machine to produce a specialized machine, such that the instructions that execute on the computer or other programmable machine create means for implementing the functions specified in the block diagrams, schematic diagrams or flowcharts. Such computer program instructions may also be stored in a computer-readable medium that when loaded into a computer or other programmable machine can direct the machine to function in a particular manner, such that the instructions stored in the computer-readable medium produce an article of manufacture including instruction means that implement the function specified in the block diagrams, schematic diagrams or flowcharts.

In addition, the computer program instructions may be loaded into a computer or other programmable machine to cause a series of operational steps to be performed by the computer or other programmable machine to produce a computer-implemented process, such that the instructions that execute on the computer or other programmable machine provide steps for implementing the functions specified in the block diagram, schematic diagram, flowchart block or step.

Accordingly, blocks or steps of the block diagram, flowchart or control flow illustrations support combinations of means for performing the specified functions, combinations of steps for performing the specified functions and program instruction means for performing the specified functions. It will also be understood that each block or step of the block diagrams, schematic diagrams or flowcharts, as well as combinations of blocks or steps, can be implemented by special purpose hardware-based computer systems, or combinations of special purpose hardware and computer instructions, that perform the specified functions or steps.

As an example, provided for purposes of illustration only, a data input software tool of a search engine application can be a representative means for receiving a query including one or more search terms. Similar software tools of applications, or implementations of embodiments of the present invention, can be means for performing the specified functions. For example, an embodiment of the present invention may include computer software for interfacing a processing element with a user-controlled input device, such as a mouse, keyboard, touch screen display, scanner, or the like. Similarly, an output of an embodiment of the present invention may include, for example, a combination of display software, video card hardware, and display hardware. A processing element may include, for example, a controller or microprocessor, such as a central processing unit (CPU), arithmetic logic unit (ALU), or control unit.

Here has thus been described a multitude of embodiments of the cycling exercise system 100, 101, and methods related thereto, which can be employed in numerous modes of usage.

The many features and advantages of the invention are apparent from the detailed specification, and thus, it is intended by the appended claims to cover all such features and advantages of the invention, which fall within the true spirit and scope of the invention.

For example, alternative embodiments can reconfigure or combine the components of the cycling exercise server 102 and the cycling exercise device 104. The components of the cycling exercise server 102 can be distributed over a plurality of physical, logical, or virtual servers. Parts or all of the components of the cycling exercise device 104 can be configured to operate in the cycling exercise server 102, whereby the cycling exercise device 104 for example can function as a thin client, performing only graphical user interface presentation and input/output functions. Alternatively, parts or all of the components of the cycling exercise server 102 can be configured to operate in the cycling exercise device 104.

Many such alternative configurations are readily apparent, and should be considered fully included in this specification and the claims appended hereto. Accordingly, since numerous modifications and variations will readily occur to those skilled in the art, the invention is not limited to the exact construction and operation illustrated and described, and thus, all suitable modifications and equivalents may be resorted to, falling within the scope of the invention.

What is claimed is:

1. A cycling exercise system, comprising:
   a) a bicycle; and
   b) a cycling exercise device;
   wherein the cycling exercise device is configured to enable a user to select a selected cycling course representation from a plurality of predetermined cycling course representations;
   such that the cycling exercise device is configured to direct the user along the selected cycling course representation and provide the user with segment exercise instructions specific to course segments of the selected cycling course representation;
   wherein each cycling course representation in the plurality of predetermined cycling course representations comprises:
      a course name;
      a course length;
      a course difficulty rating; and
      a list of the course segments, wherein each course segment comprises:
         a segment identifier;
         a starting coordinate; and
         a list of associated exercises, each including:
            an exercise name;
            an exercise difficulty level; and
            associated exercise instructions.

2. The cycling exercise system of claim 1, wherein the cycling exercise device is mounted on the bicycle.

3. The cycling exercise system of claim 1, further comprising:
   a cycling exercise server, which is configured to store the plurality of predetermined cycling course representations;
   wherein the cycling exercise device is configured to retrieve the selected cycling course representation in the plurality of predetermined cycling course representations from the cycling exercise server.

4. The cycling exercise system of claim 3, wherein the cycling exercise server further comprises:
a) a processor;
b) a non-transitory memory;
c) an input/output component; and
d) a course database, which stores the plurality of predetermined cycling course representations; all connected via
e) a data bus.

5. The cycling exercise system of claim 1, wherein the cycling exercise device further comprises:
a) a processor;
b) a non-transitory memory;
c) an input/output component; and
d) an exercise controller, which is configured to direct the user along the selected cycling course representation; all connected via
e) a data bus.

6. The cycling exercise system of claim 1, wherein each cycling course representation in the plurality of predetermined cycling course representations further comprises:
a list of trainers.

7. The cycling exercise system of claim 1, wherein each associated exercise in the list of associated exercises further comprises:
an exercise category, which comprises at least one of endurance, strength, and interval.

8. The cycling exercise system of claim 1, wherein each course segment in the list of the course segments further comprises:
a list of associated music segments, each comprising:
a song name;
an artist name; and a
song recording, which is playable by the exercise device.

9. The cycling exercise system of claim 1, wherein the cycling exercise device is configured to calculate a list of available courses from the plurality of predetermined cycling course representations, such that the available courses are within a predetermined maximum distance, such that a minimum distance from a current location to a closest starting coordinate of a closest course segment is within the predetermined maximum distance.

10. The cycling exercise system of claim 9, wherein the cycling exercise device is configured to enable the user to select a selected available course from the list of available courses, such that the cycling exercise device is configured to provide directions from the current location to the closest starting coordinate of the closest course segment of the selected available course.

11. A cycling exercise device, which is configured to enable a user to select a selected cycling course representation from a plurality of predetermined cycling course representations;
such that the cycling exercise device is configured to direct the user along the selected cycling course representation and provide the user with segment exercise instructions specific to course segments of the selected cycling course representation;
wherein each cycling course representation in the plurality of predetermined cycling course representations comprises:
a list of the course segments, wherein each course segment comprises:
a starting coordinate; and
a list of associated exercises, each comprising:
associated exercise instructions;
wherein the cycling exercise device is configured to calculate a list of available courses within a predetermined maximum distance, such that a minimum distance from a current location to a closest starting coordinate of a closest course segment is within the predetermined maximum distance.

12. The cycling exercise device of claim 11, further comprising:
a) a processor;
b) a non-transitory memory;
c) an input/output component; and
d) an exercise controller, which is configured to direct the user along the selected cycling course representation; all connected via
e) a data bus.

13. The cycling exercise device of claim 11, wherein each cycling course representation in the plurality of predetermined cycling course representations further comprises:
a) a course name;
b) a course length; and
c) a course difficulty rating;
wherein each course segment further comprises:
a segment identifier; and
wherein each associated exercise further comprises:
an exercise name; and
an exercise difficulty level.

14. The cycling exercise device of claim 11, wherein the cycling exercise device is configured to enable the user to select a selected available course from the list of available courses, such that the cycling exercise device is configured to provide directions from the current location to the closest starting coordinate of the closest course segment of the selected available course.

15. A method of cycling exercise, comprising:
directing a user around a selected cycling course representation, which is selected from a plurality of predetermined cycling course representations; and providing the user with segment exercise instructions specific to course segments of the selected cycling course representation;
wherein each cycling course representation in the plurality of predetermined cycling course representations comprises:
a course name;
a course length;
a course difficulty rating; and
a list of the course segments, wherein each course segment comprises:
a segment identifier;
a starting coordinate; and
a list of associated exercises, each including:
an exercise name;
an exercise difficulty level; and
associated exercise instructions;
calculating a list of available courses from the plurality of predetermined cycling course representations, such that the available courses are within a predetermined maximum distance, such that a minimum distance from a current location to a closest starting coordinate of a closest course segment is within the predetermined maximum distance;
selecting the selected cycling course representation from the list of available courses; and directing the user from the current location to the closest starting coordinate of the closest course segment of the selected cycling course representation.

* * * * *